United States Patent [19]
Hawkinson et al.

[11] Patent Number: 6,050,136
[45] Date of Patent: Apr. 18, 2000

[54] TIRE DEFECT DETECTION EMPLOYING ELECTRICAL ARCING

[75] Inventors: Raymond P. Hawkinson, Minneapolis; Dennis W. Newman, St. Paul, both of Minn.

[73] Assignee: Paul E. Hawkinson Company, Minneapolis, Minn.

[21] Appl. No.: 09/061,537

[22] Filed: Apr. 16, 1998

Related U.S. Application Data

[60] Provisional application No. 60/041,992, Apr. 16, 1997.

[51] Int. Cl.⁷ .................................................. G01M 17/02
[52] U.S. Cl. ............................................ 73/146; 324/558
[58] Field of Search .............................. 73/146; 324/558

[56] References Cited

U.S. PATENT DOCUMENTS

| | | |
|---|---|---|
| 4,516,068 | 5/1985 | Hawkinson, Jr. et al. . |
| 4,520,307 | 5/1985 | Weiss et al. . |
| 4,936,138 | 6/1990 | Cushman et al. ..................... 73/146 |

OTHER PUBLICATIONS

"Hawkinson NDT® Combo–2 Operator Manual", Feb. 20, 1995, Hawkinson Treading, Inc., Minneapolis, MN (13 pgs).

*Primary Examiner*—Joseph L. Felber
*Attorney, Agent, or Firm*—Merchant & Gould P.C.

[57] ABSTRACT

An apparatus for testing a tire. The tire has sidewalls and a tread portion. The tread portion has inner and outer surfaces. The apparatus comprises a tire lift. The tire lift has a main frame and a subframe. The subframe engages the main frame and is movable in a vertical direction. First and second drive rollers are operably connected to the subframe and arranged to support the tread portion. A stabilization roller is operably connected to the tire lift. The stabilization roller is arranged and configured to be placed proximal to one of the sidewalls. First and second electrodes are operably connected to the tire lift. The first and second electrodes are arranged and configured to be positioned on opposite sides of the tread portion. A power supply is arranged and configured to create an electrical potential between the first and second electrodes.

9 Claims, 4 Drawing Sheets

TIRE DEFECT DETECTION EMPLOYING ELECTRICAL ARCING

REFERENCE TO CO-PENDING APPLICATION

This application is a continuation of provisional application No. 60/041,992, which was filed on Apr. 16, 1997 and entitled Improved Tire Defect Tester, the disclosure of which is hereby incorporated by reference.

TECHNICAL FIELD

The present invention relates to a tire defect tester, and more particularly, to a tire defect tester that uses electrical arcing to detect a defect.

BACKGROUND

New tires are expensive. As a result, replacing and maintaining tires can be an economic burden for those who manage a large fleet vehicles or otherwise place excessive wear on their tires. Replacing tires can also be a burden for those of modest means.

As a result, it is becoming increasingly important to repair damaged tires rather than replace them with new tires. Repairing a damaged tire is usually very simple and inexpensive, especially repairing simple holes or objects that become embedded in the treaded portion of the tire.

Diagnosis is the first step in repairing a damaged tire. It is necessary to ascertain if any foreign objects are embedded in the tread portion of the tire or if any cracks, fissures, or holes exist therein. The prior art has typically relied upon visual inspection in order to make this determination. If such defects are found to exist, the tire can be repaired. If the defect is not found, the tire must be replaced.

There are several techniques for inspecting a tire. One such technique is visual inspection, which tends to be slow and time consuming. More importantly, however, this method for searching for defects is, at best, unreliable. With this method, a tire is rotated on a mounting stand, and an inspector visually observes the tread portion of the tire as it passes beneath his gaze. The difficulties is that some defects are so minute that they escape the detection of even a trained, experienced observer. Even these defects can weaken the tire and become a hazard to vehicles operating at high rates of speed.

In an attempt to solve some of the problems inherent in visual inspection, other types of testing techniques have been devised. One such method involves over inflating a tire and either immersing the tire in a fluid or applying a fluid to the outer surface thereof. A leak of air through an orifice or fissure can be detected visually more readily by the observation of a bubbling effect, which will occur at the location of the defect. This method, however, will not detect defects other than well defined holes that pass all the way through the treaded portion of a tire.

Another inspection technique uses a wand that has an electrode and a high voltage power supply. An inspector passes the wand over the surface of the tire and watches for any arcing that occurs between the electrode and nails embedded in the tire or holes that expose the steel belt from the tire. The difficulty with such wands, is that the inspector may not pass the electrode over the entire surface of the tire's tread portion and thus fail to detect some defects. Another shortcoming is that such a wand will not detect a simple hole or puncture mark if there is not a metal object or belt embedded in the tire.

More complex systems for detecting tire defects also exist. In one such system, the tread portion of a tire is sandwiched between a pair of electrodes across which a high voltage electrical potential is generated. With this system, if objects such as nails are embedded in the tread portion of the tire or if defects such as orifices or fissures exist, the voltage applied across the electrodes will cause arcing at the point of foreign object or defect. Such a device typically rotates the tire such that the tread portion passes between the electrodes. Additionally, such an apparatus typically includes an electronics package whereby as a defect is detected by arcing across the electrodes, rotation of the tire is stopped, and an alarm is actuated. Pinpointing the location of the defect is, thereby, facilitated.

Such advanced machines are typically complex, large, and expensive. They are appropriate for high volume retreading operations that inspect and retread a large number of tires. Additionally, these advanced machines are typically too expensive and too large for smaller garages and tire shops that do not inspect and repair tires in mass.

Therefore, there is a need for an improved tire defect tester. Such an improved tire defect tester would be inexpensive and simple to use. Such a tire defect tester would also ensure that the entire treaded portion of the tire is thoroughly inspected.

SUMMARY

One possible embodiment of the present invention is directed to an apparatus for testing a tire. The tire has sidewalls and a tread portion, and the tread portion has inner and outer surfaces. The apparatus comprises a tire lift. The tire lift has a main frame and a subframe that engages the main frame. The subframe is movable in a vertical direction. First and second drive rollers are operably connected to the subframe and arranged to support the tread portion. A stabilization roller is operably connected to the tire lift. The stabilization roller is arranged and configured to be placed proximal to one of the sidewalls. First and second electrodes are operably connected to the tire lift. The electrodes are arranged and configured to be positioned on opposite sides of the tread portion. A power supply is arranged and configured to create an electrical potential between the first and second electrodes.

Another possible embodiment of the invention is directed to an apparatus that comprises a tire lift having a main frame and a subframe. The subframe engages the main frame and is movable in a vertical direction. First and second drive rollers are operably connected to the subframe and arranged to support the tread portion. First and second horizontally spaced rollers are operably connected to the wheel lift. The first horizontally spaced roller is arranged to be positioned proximal to one sidewall, and the second horizontally roller is configured to be positioned proximal to the other sidewall. First and second electrodes are operably connected to the tire lift. The first and second electrodes are arranged and configured to be positioned on opposite sides of the tread portion. A power supply is arranged and configured to create an electrical potential between the first and second electrodes.

DETAILED DESCRIPTION

Various embodiments of the present invention are described in detail with reference to the drawings. Reference to the various embodiments does not limit the scope of the invention, which is limited only by the scope of the claims attached hereto.

Figure 1:
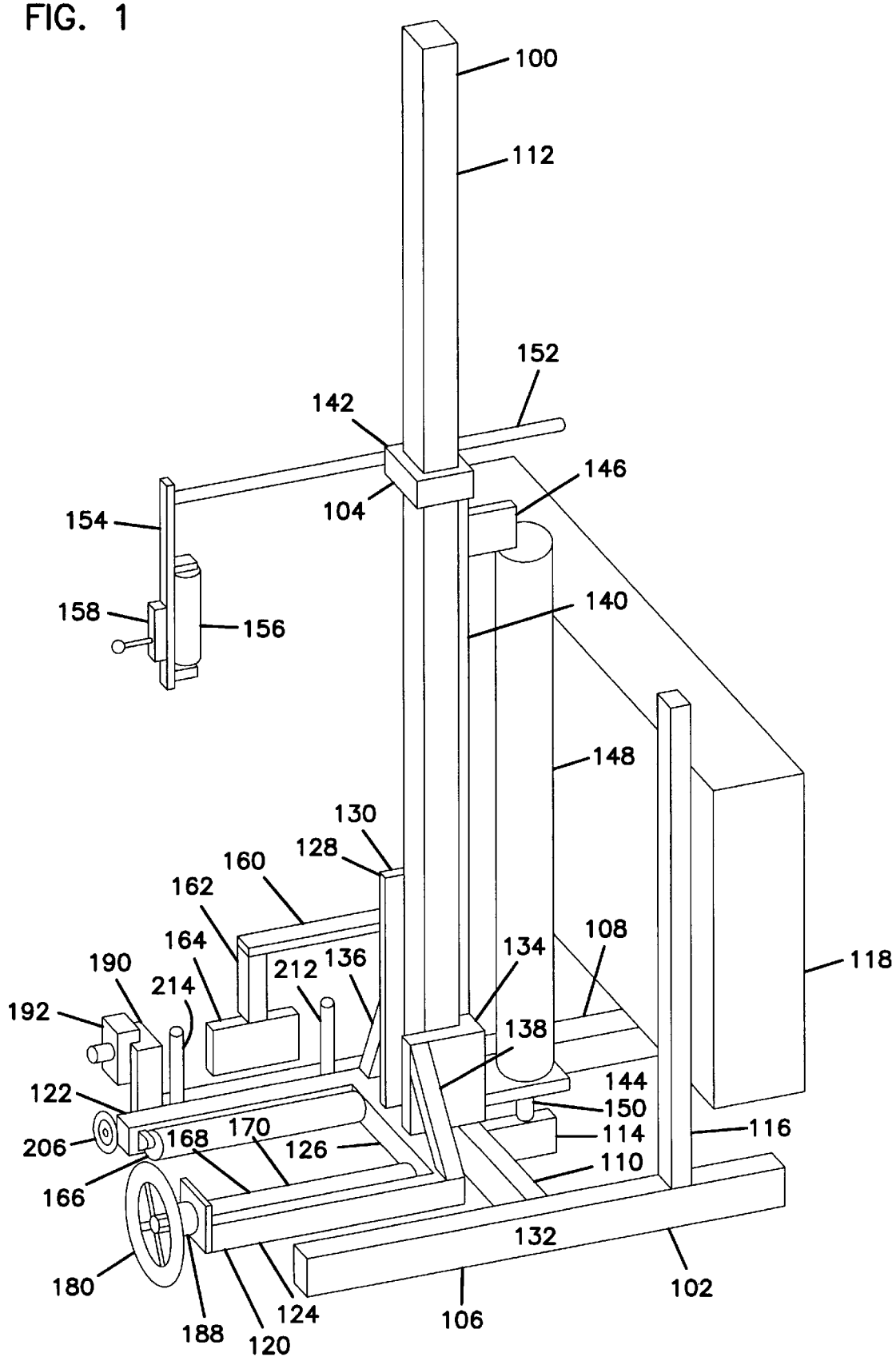
FIG. 1 is a top perspective view of one possible embodiment of a tire defect tester that includes the present invention.

Referring to FIG. 1, the tire defect tester has a tire lift 100. One possible embodiment of the tire lift 100 has a main frame 102 and a subframe 104. The main frame 102 has two parallel base members 106 and 108 that are connected by an intermediate member 110. The intermediate member 110 is perpendicular to the base members 106 and 108. A vertical support beam 112 projects upward from the intermediate member 110. The vertical support beam 112 has a height sufficient that the subframe 104, and hence the tire being tested, can be raised to eye level for easy inspection. A flange 114 projects rearward from the intermediate member 110.

Two control panel supports 116 and (not shown) project upward from each of the base members 106 and 108, respectively, and a control panel 118 is mounted to the control panel supports. The control panel 118 houses a power supply and electronics for charging electrodes, which are described in more detail below.

The subframe 104 slidably engages the main frame 102. The subframe 104 includes a U-shaped chassis 120 having first and second support beams 122 and 124 that are parallel to one another. An intermediate portion 126 is perpendicular to and extends between the first and second support beams 122 and 124.

A first collar 128 has three sides 130, 132 and 134. First and second sides 130 and 132 are positioned on opposite sides of the vertical support beam 112 and are attached to the intermediate member 126 of the subframe 104. The first side 130 is taller than the second side 132. The third side 134 extend between the first and second sides 132 and 134. The third side 134 is on an opposite side of the vertical support beam 112 from the intermediate member 126 of the U-shaped chassis 120. In this configuration, the first collar 128 holds the U-shaped chassis 120 to the vertical support frame 112. In order to add structural rigidity, angular reinforcement beams 136 and 138 extend between the first and second sides 130 and 132 of the collar 128 and the intermediate portion 126 of the U-shaped chassis 120.

A vertical subframe beam 140 extends upward from the third side 134 of the first collar 128 and is positioned proximal to a rear surface of the vertical support beam 112 of the main frame 102. A second collar 142 is mounted around the vertical support beam 112 of the main frame 102 and is attached to the vertical subframe beam 140.

A first cylinder flange 144 extends rearward form the third side 134 of the first collar 128. A second cylinder flange 146 extends rearward from the vertical subframe beam 140 and is proximal to the second collar 142. A hydraulic cylinder 148 is vertically oriented and extend between the first and second cylinder flanges 144 and 146. The hydraulic cylinder 148 has a cylinder arm 150 that projects downward and passes through the first cylinder flange 144. The cylinder arm 150 is attached to the flange 114 of the main frame 102.

A horizontally oriented bar 152 is attached to the second collar 142, and has a bracket 154 extending downward from one end. A vertical stabilization roller 156 is mounted to the bracket 154 and faces rearward toward the vertical support beam 112 of the main frame 102. The bar 152 slidably engages the second collar 142 so that the position of the vertical stabilization roller 156 is adjustable.

A hydraulic valve 158 is mounted on the front of the bracket 154 and is connect to the hydraulic cylinder 148 via hoses (not shown). An operator can actuate the valve 158 to cause the cylinder arm 150 to either retract into or extend from the hydraulic cylinder 148. Causing the cylinder arm 150 to extend from the hydraulic cylinder 148 will cause the first and second collars 128 and 142 to slide along the vertical support beam 112 of the main frame 102, and thus the subframe 104 to move upward. Likewise, causing the cylinder arm 150 to retract will cause the subframe 104 to move downward relative to the main frame 102. In order to aid movement of the subframe 104, bushings or bearings can be placed between the first and second collars 128 and 142 and the vertical support beam 112.

An electrode bracket 160 is pivotally connected to the first side 130 of the first collar 128, and is positioned toward the top edge of the first side 130. An insulating bracket 162 is detachably connected to the projecting end of the electrode bracket 160, and a first electrode 164 is mounted to the insulating bracket 162. The first electrode 164 is electrically connected to the control panel 118 with wires (not shown). The first electrode 164 is described in more detail below. An advantage of pivotally mounting the electrode bracket 160 is that the position of the first electrode 164 can be adjusted slightly to ensure good contact with the inner surface of a tire's tread portion. Additionally, an interlock (not shown) can be operatively connected between the first electrode 164 and the electrode bracket 160. The interlock would prevent the first electrode 164 from being energized when not properly attached to the electrode bracket 160.

First and second drive rollers 166 and 168 are mounted to the to the first and second support beams 122 and 124, respectively, of the U-shaped chassis 120 with bearing assemblies. The first roller 166 is made from an insulating material such as rubber. Rubber is advantageous because it provides traction with a tire. The second roller 168 has ribs extending along its length to provide traction with a tire that is mounted in the tire lift. Additionally, the second roller 168 is formed from a metallic roller to form a second electrode 170. The second roller 168 is then electrically connected to the circuitry in the control panel 118 and is grounded. This configuration is advantageous because the tread portion of a tire can rest on the first and second rollers 166 and 168.

Figure 2:
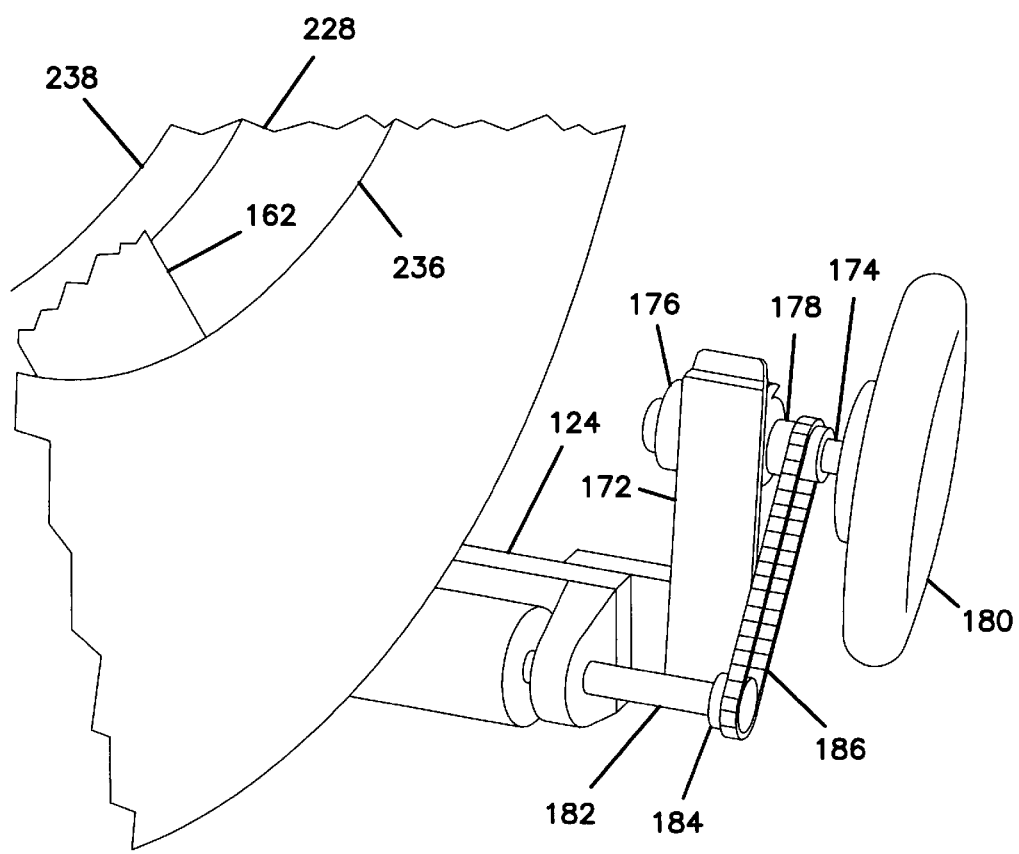
FIG. 2 is a fragmentary view illustrating a drive roller and crank assembly shown in FIG. 1.

Referring to FIGS. 1 and 2, a bracket 172 is mounted on the end of the second support beam 124 of the U-shaped chassis 120. A spindle 174 is mounted to the bracket 172 by a bearing assembly 176. A first sprocket 178 and a first hand wheel 180 are mounted on the spindle 174. In turn, the second drive roller 168 has an axle 182 that extends outward from one end. A second sprocket 184 is mounted on the axle 182 of the second drive roller 168. A chain 186 extend around the first and second sprockets 178 and 184. Additionally, a cowling 188 (not shown in FIG. 2) provides protective covering for the chain 186, the first sprocket 178, and the second sprocket 184.

In an alternative embodiment, a motor (not shown) is mounted to the subframe 104 in place of the first hand wheel 180. The motor would permit automatic rotation of the second drive roller 168, and hence automatic rotation of the tire.

Figure 3:
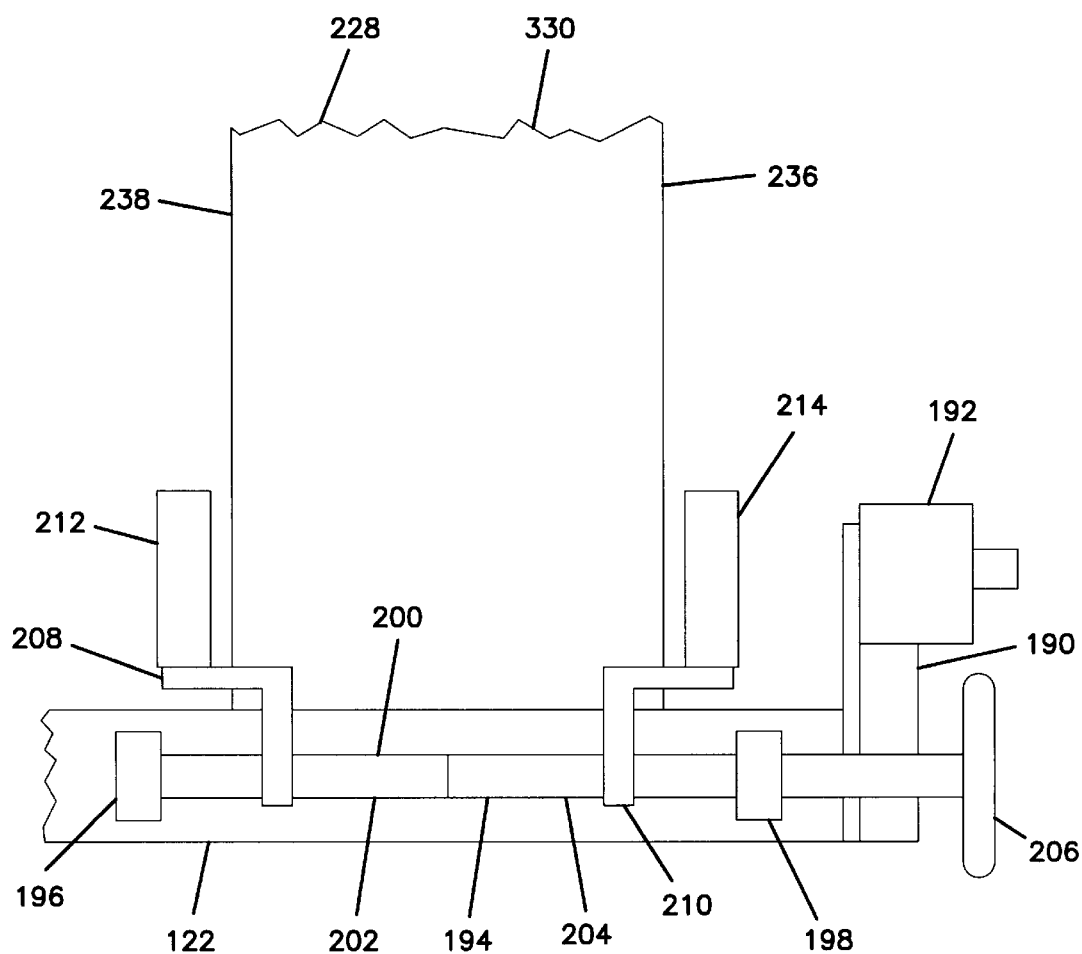
FIG. 3 is a fragmentary view illustrating a roller assembly shown in FIG. 1.

Referring to FIGS. 1 and 3, a bracket 190 is mounted on the end of the first support beam 122 of the U-shaped chassis 120 and an electrical switch 192 is mounted on the bracket 190. The electrical switch is connected to the power supply and circuitry in the control panel via wires (not shown). Actuating the electrical switch 192 will energize the first and second electrodes 164 and 170.

A screw mechanism 194 is also rotatably mounted to the first support beam 122 of the U-shaped chassis 120 by first and second bearing assemblies 196 and 198. The screw mechanism 194 has a treaded rod 200 that has first and second portions 202 and 204. The first portion 202 has threads in one direction, and the second portion 204 has threads in an opposite direction. A second hand wheel 206 is mounted on the end of the threaded rod 200.

A first roller bracket 208 is mounted to the first portion 202 of the treaded rod 200, and a second roller bracket 210 is mounted to the second portion 204 of the thread rod 200. First and second rollers 212 and 214 are mounted to the first and second brackets 208 and 210, respectively, and are then horizontally spaced. The first and second rollers 212 and 214 are arranged and configured to be positioned proximal to the sidewalls of a tire. The distance between the first and second rollers 212 and 214 is adjustable by turning the second hand wheel 206. Turning the second hand wheel 206 in one direction will cause the first and second rollers 212 and 214 to move closer together, and turning the second hand wheel 206 in an opposite direction will cause the first and second rollers 212 and 214 to move farther apart.

Figure 4:
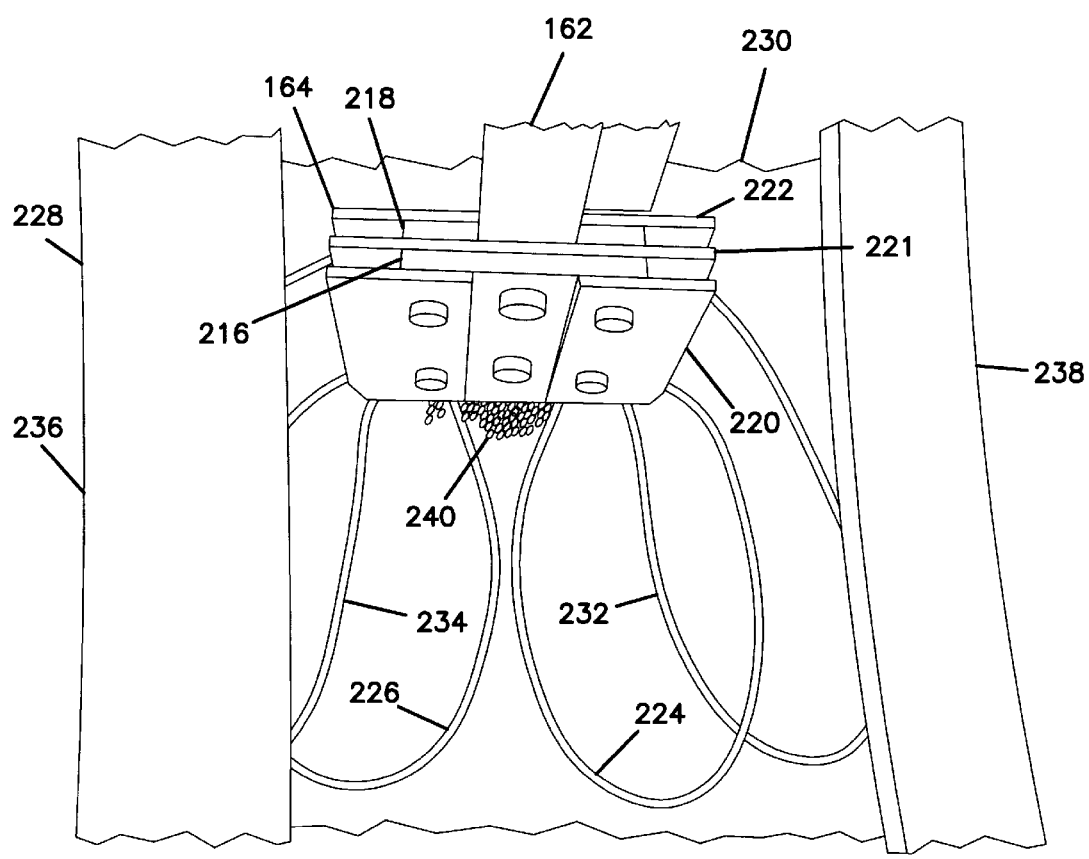
FIG. 4 is a fragmentary view illustrating a first electrode assembly shown in FIG. 1.

Referring now to FIG. 4, the first electrode 164 has two conductive plates 216 and 218 that are isolated by insulators 220, 221 and 222 and are mounted to the insulating bracket 162. A first pair of wire lobes 224 and 226 are in electrical communication with the first conductive plate 216. The first pair of wire lobes 224 and 226 project downward so that they engage the inner surface of the tire's 228 tread portion 230. A second pair of wire lobes 232 and 234 are in electrical communication with the second conductive plate 218 and project from opposite sides of the electrode 164. In this configuration, the second pair of wire lobes 232 and 234 engage the region between the tire's tread portion 230 and sidewalls 236 and 238.

Additionally, a series of beaded chains 240 hang downward from the electrode 164. The first pair of lobed wires 224 and 226, the second pair of lobed wires 132 and 134, and the beaded chains 240 are all electrified when the first electrode 164 is energized. One type of electrode that can be used is model no. INTER-NDT-LT (called Probe—for Light Truck), which is manufactured by the Paul E. Hawkinson Company, having its principle place of business in Minneapolis, Minn.

In use, an operator will lower the subframe 104 so that the U-shaped chassis 120 is proximal to the base members 106 and 108 of the main frame 102. The worker then removes the first electrode 164 and insulating bracket 162 from the electrode bracket 160 to clear room for a tire. The operator rolls a tire onto the U-shaped chassis 120 so that the tread portion 230 of the tire 228 rests on the first and second drive rollers 166 and 168.

In this position, the stabilization roller 156 is proximal to the outer sidewall 236 of the tire 228. The operator can adjust the position of the stabilization roller 156 by sliding the bar 152 relative to the second collar 142. Additionally, the tire 228 is positioned between the first and second horizontally spaced rollers 212 and 214. The operator can then rotate the second hand wheel 206 and adjust the distance between the first and second horizontally spaced rollers 212 and 214. The stabilization roller 156, as well as the first and second horizontally spaced rollers 212 and 214 should be proximal to the sidewalls 236 and 236 of the tire 228, but not necessarily touching the tire 228.

In this configuration, the rollers 152, 212, and 214 stabilize the tire 228 while it is rotating, as described below. Stabilizing the tire 228 is important because the tire 228 may wobble because of conditions such as uneven wear in the treads or because of the narrow width of the tire 228 relative to its height. Because most tires have similar sizes, the operator typically does not need to adjust the rollers 156, 212 and 214 prior to testing each tire. An adjustment needs to be made only if there is a relatively drastic change in the size of tires being tested.

After the tire 228 is mounted, the operator will actuate the hydraulic valve 158 and cause the cylinder arm 150 to extend, thereby raising the tire 228. The operator typically raises the tire 228 to a level where he/she can easily peer into the tire 228 or observe the outer surface of the tread portion 230 proximal to the second drive roller 168. The operator then positions the first electrode 164 in the tire 228 and attaches the insulating bracket 162 to the electrode bracket 160. In this position, the interlock will permit the electrodes 164 and 170 to be energized. An alternative embodiment includes a mirror (not shown) operably connected to the subframe 104 and positioned so that the operator can observe arcing from the second electrode 170 without bending over.

Once the first electrode 164 is in place, the operator can actuate the switch 192 and energize the first and second electrodes 164 and 170. The operator turns the first hand wheel 180 to rotate the tire 228, which moves the inner surface of the tread portion 230 against the first electrode 164 and the outer portion of the tread portion 230 against the second electrode 170. The operator watches for arcing that occurs from either one of the electrodes 164 or 170. The operator can also listen for arcing, which will make a poping or cracking noise.

When an arc occurs, the operator will stop rotating the tire 228 and release the switch 192, which causes the electrodes 164 and 170 to deenergize. The operator can then safely mark the location of the defect for repair. After marking the operator reenergizes the electrodes 164 and 170 and continues to rotate the tire 228.

This process is continued until the entire tire 228 has been inspected. The operator then lowers the subframe 104, detaches the first electrode 164, and rolls the tire 228 off the tire lift 100.

The various embodiments described above are provided by way of illustration only and should not be construed to limit the invention. Those skilled in the art will readily recognize various modifications and changes that may be made to the present invention without strictly following the example embodiments and applications illustrated and described herein, and without departing from the true spirit of the present invention, which is set forth in the following claims.

The claimed invention is:

1. An apparatus for testing a tire, the tire having sidewalls and a tread portion, the tread portion having inner and outer surfaces, the apparatus comprising:

a tire lift, the tire lift having a frame and a subframe engaging the main frame, the subframe being movable in a vertical direction;

first and second drive rollers operably connected to the subframe and arranged to support the tread portion;

a stabilization roller operably connected to the tire lift, the stabilization roller arranged and configured to be placed proximal to one of the sidewalls;

first and second electrodes operably connected to the tire lift, the electrodes arranged and configured to be positioned on opposite sides of the tread portion; and a power supply arranged and configured to create an electrical potential between the first and second electrodes.

2. The apparatus of claim 1 wherein:

the first electrode is configured to be positioned proximal to the inner surface of the tread portion;

the second electrode is configured to be positioned proximal to the outer surface of the tread portion; and at least one of the drive rollers is at least partially formed from a conductive material and is configured to form the second electrode.

3. The apparatus of claim 1 further comprising first and second horizontally spaced rollers operably connected to the tire lift, the first horizontally spaced roller arranged to be positioned proximal to the first sidewall, and the second horizontally spaced roller configured to be positioned proximal to the second sidewall.

4. The apparatus of claim 3 wherein the distance between the first and second horizontally spaced rollers is adjustable.

5. The apparatus of claim 1 further comprising a hydraulic cylinder connected between the main frame and the subframe, the hydraulic cylinder being arranged and configured to move the subframe in the vertical direction.

6. The apparatus of claim 1 further comprising a hand crank operably connected to at least on e of the drive rollers.

7. The apparatus of claim 1 further comprising a motor operably connected to at least one of the drive rollers.

8. An apparatus for testing a tire, the tire having sidewalls and a tread portion, the tread portion having inner and outer surfaces, the apparatus comprising:

a tire lift, the tire lift having a frame and a subframe engaging the main frame, the subframe being movable in a vertical direction;

first and second drive rollers operably connected to the subframe and arranged to support the tread portion;

first and second horizontally spaced rollers operably connected to the tire lift, the first horizontally spaced roller arranged to be positioned proximal to the first sidewall, and the second horizontally spaced roller configured to be positioned proximal to the second sidewall;

first and second electrodes operably connected to the tire lift, the electrodes arranged and configured to be positioned on opposite sides of the tread portion; and a power supply arranged and configured to create an electrical potential between the first and second electrodes.

9. An apparatus for testing a tire, the tire having sidewalls and a tread portion, the tread portion having inner and outer surfaces, the apparatus comprising:

a tire lift, the tire lift having a frame and a subframe engaging the main frame, the subframe being movable in a vertical direction;

a hydraulic cylinder connected between the main frame and the subframe, the hydraulic cylinder being arranged and configured to move the subframe in the vertical direction;

first and second drive rollers operably connected to the subframe and arranged to support the tread portion;

a stabilization roller operably connected to the tire lift, the stabilization roller arranged and configured to be placed proximal to one of the sidewalls;

first and second horizontally spaced rollers operably connected to the tire lift, the first horizontally spaced roller arranged to be positioned proximal to the first sidewall, and the second horizontally spaced roller configured to be positioned proximal to the second sidewall;

first and second electrodes operably connected to the tire lift, the electrodes arranged and configured to be positioned on opposite sides of the tread portion; and a power supply arranged and configured to create an electrical potential between the first and second electrodes.

* * * * *